(12) United States Patent
Muller et al.

(10) Patent No.: US 11,969,158 B2
(45) Date of Patent: *Apr. 30, 2024

(54) INTRODUCER SHEATH ASSEMBLY FOR CATHETER SYSTEMS AND METHODS OF USING SAME

(71) Applicant: TC1 LLC, St. Paul, MN (US)

(72) Inventors: Paul Muller, San Carlos, CA (US);
Keif Fitzgerald, San Jose, CA (US);
Ted Su, Sunnyvale, CA (US); Michael Butler, Alameda, CA (US)

(73) Assignee: TC1 LLC, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/325,770

(22) Filed: May 30, 2023

(65) Prior Publication Data

US 2023/0301642 A1    Sep. 28, 2023

Related U.S. Application Data

(63) Continuation of application No. 16/864,545, filed on May 1, 2020, now Pat. No. 11,690,606.

(Continued)

(51) Int. Cl.
*A61M 60/585* (2021.01)
*A61B 17/00* (2006.01)
(Continued)

(52) U.S. Cl.
CPC ....... *A61B 17/00234* (2013.01); *A61M 60/13* (2021.01); *A61M 60/174* (2021.01);
(Continued)

(58) Field of Classification Search
CPC .... A61B 17/00234; A61B 2017/00243; A61B 2017/00336; A61B 2017/00867;
(Continued)

(56) References Cited

U.S. PATENT DOCUMENTS

| 5,207,648 A | 5/1993 | Gross |
| 5,290,310 A | 3/1994 | Makower et al. |

(Continued)

FOREIGN PATENT DOCUMENTS

JP    2016163667 A    9/2016

OTHER PUBLICATIONS

International Preliminary Report on Patentability for PCT/US2020/030989 dated Nov. 11, 2011, 9 pgs.

*Primary Examiner* — Ankit D Tejani
*Assistant Examiner* — Joshua Brendon Solomon
(74) *Attorney, Agent, or Firm* — Armstrong Teasdale LLP

(57) ABSTRACT

A catheter system includes a catheter, an introducer sheath, and a tubular plug. The catheter comprises an elongate body having an expandable medical device coupled with a distal end thereof. The introducer sheath comprises an elongate body defining a lumen therein. The introducer sheath is disposed over the catheter to form a gap therebetween. The tubular plug comprises an elongate body and extends through the lumen of the introducer sheath. The tubular plug is disposed between the catheter and the introducer sheath to occlude the gap. Further, the tubular plug is releasably fixed relative to the introducer sheath such that the tubular plug is removable from the lumen to allow the expandable medical device to pass therethrough.

20 Claims, 9 Drawing Sheets

Related U.S. Application Data

(60) Provisional application No. 62/841,602, filed on May 1, 2019.

(51) Int. Cl.

| | |
|---|---|
| *A61M 60/13* | (2021.01) |
| *A61M 60/174* | (2021.01) |
| *A61M 60/216* | (2021.01) |
| *A61M 60/414* | (2021.01) |
| *A61M 60/416* | (2021.01) |
| *A61M 60/808* | (2021.01) |
| *A61M 60/857* | (2021.01) |
| *A61M 60/865* | (2021.01) |

(52) U.S. Cl.
CPC ........ *A61M 60/216* (2021.01); *A61M 60/414* (2021.01); *A61M 60/416* (2021.01); *A61M 60/585* (2021.01); *A61M 60/808* (2021.01); *A61M 60/857* (2021.01); *A61M 60/865* (2021.01); *A61B 2017/00243* (2013.01); *A61B 2017/00336* (2013.01); *A61B 2017/00867* (2013.01)

(58) Field of Classification Search
CPC .............. A61M 60/416; A61M 60/585; A61M 60/808; A61M 60/857; A61M 60/865; A61M 2039/062; A61M 25/0097; A61M 25/0662; A61M 39/0606; A61M 2025/0004; A61M 2025/0018
See application file for complete search history.

(56) References Cited

U.S. PATENT DOCUMENTS

| | | |
|---|---|---|
| 6,641,564 B1 | 11/2003 | Kraus |
| 10,149,932 B2 | 12/2018 | McBride et al. |
| 11,690,606 B2 * | 7/2023 | Muller .............. A61M 25/0097 600/16 |
| 2004/0147877 A1 | 7/2004 | Heuser |
| 2012/0083740 A1 | 4/2012 | Chebator et al. |
| 2013/0317439 A1 | 11/2013 | Ellingwood et al. |
| 2019/0070394 A1 | 3/2019 | Appling et al. |

* cited by examiner

INTRODUCER SHEATH ASSEMBLY FOR CATHETER SYSTEMS AND METHODS OF USING SAME

CROSS-REFERENCE TO RELATED APPLICATIONS

This application is a continuation of U.S. patent application Ser. No. 16/864,545, filed May 1, 2020, which claims priority to U.S. provisional patent application Ser. No. 62/841,602, filed May 1, 2019, the disclosures of which are incorporated by reference herein in their entirety.

BACKGROUND OF THE DISCLOSURE a. Field of the Disclosure

The present disclosure relates generally to medical devices that are used in the human body. In particular, the present disclosure relates to an introducer sheath assembly for use with a catheter or other medical devices to improve the overall performance of the catheter or other medical devices during a medical procedure.

b. Background

Heart disease is a major health problem that claims many lives per year. After a heart attack or other major cardiac event, a small number of patients can be treated with medicines or other non-invasive treatment. A significant number of other patients can recover from a heart attack or other cardiac event if provided with mechanical circulatory support in a timely manner.

In one conventional approach for treating patients, a blood pump is inserted into a heart chamber, such as into the left ventricle of the heart and the aortic arch, to assist the pumping function of the heart. Other known conventional applications involve providing for pumping venous blood from the right ventricle to the pulmonary artery for support of the right side of the heart. The object of the pump is to reduce the load on the heart muscle for a period of time allowing the affected heart muscle to recover and heal. Blood pumps may also be used in some cases for percutaneous coronary intervention. In some cases, surgical insertion may potentially cause additional stresses in heart failure patients.

When a catheter is inserted into the body of a patient, an introducer, typically formed of a thin walled polymeric tube, is placed through the site of the incision directly into the blood vessel. The catheter is then inserted (i.e., introduced) through the introducer into the blood vessel. After the catheter has been extended to its target location, the introducer may remain in place until the catheter is removed. In some instances, this can be several hours or even several days.

SUMMARY OF THE DISCLOSURE

The present disclosure is directed to a catheter system that includes a catheter, an introducer sheath, and a tubular plug. The catheter comprises an elongate body having an expandable medical device coupled with a distal end thereof. The introducer sheath comprises an elongate body defining a lumen therein. The introducer sheath is disposed over the catheter to form a gap therebetween. The tubular plug comprises an elongate body and extends through the lumen of the introducer sheath. The tubular plug is disposed between the catheter and the introducer sheath to occlude the gap. Further, the tubular plug is releasably fixed relative to the introducer sheath such that the tubular plug is removable from the lumen to allow the expandable medical device to pass therethrough.

The present disclosure is further directed to an introducer sheath assembly that includes a valve, an introducer sheath, and a tubular plug. The valve comprises a valve body defining an elongate passage therethrough. The introducer sheath protrudes from the valve body distal end and includes an elongate body defining a lumen. The tubular plug extends through each of the elongate passage and the lumen of the introducer sheath. A distal end of the tubular plug protrudes from a distal end of the introducer sheath. Further, the tubular plug is releasably fixed relative to the introducer sheath such that the tubular plug is removable from the lumen.

DETAILED DESCRIPTION OF THE DISCLOSURE

The present disclosure is directed to introducer sheath assemblies for use with catheters and/or catheter systems that facilitate reducing obstructions or occlusions to blood flow while the catheter is positioned within a patient. In particular, the introducer sheath assemblies of the present disclosure allow for the catheter and/or catheter system to have a reduced-diameter proximal section to reduce obstructions to blood flow. For example, the introducer sheath assemblies described herein are configured to seal an opening at the incision site following removal of the initial introducer sheath, and are further configured to substantially seal or occlude a gap formed between the introducer sheath assembly and the catheter. Consequently, catheters and/or catheter systems used with the introducer sheath assemblies of the present disclosure may have a reduced-diameter proximal section, and thereby reduce obstructions to blood flow. Moreover, the introducer sheath assemblies described herein are configured to allow larger-diameter portions of the catheter, such as expandable medical devices coupled at a distal end of the catheter, to pass therethrough. For example, embodiments of the introducer sheath assemblies include a removable plug that substantially fills or occludes the gap formed between the introducer sheath assembly and the catheter when the plug is connected to the introducer sheath assembly, and that, once removed from the introducer sheath assembly, exposes a relatively large diameter lumen that allows passage of larger-diameter portions of the catheter.

Figure 1:
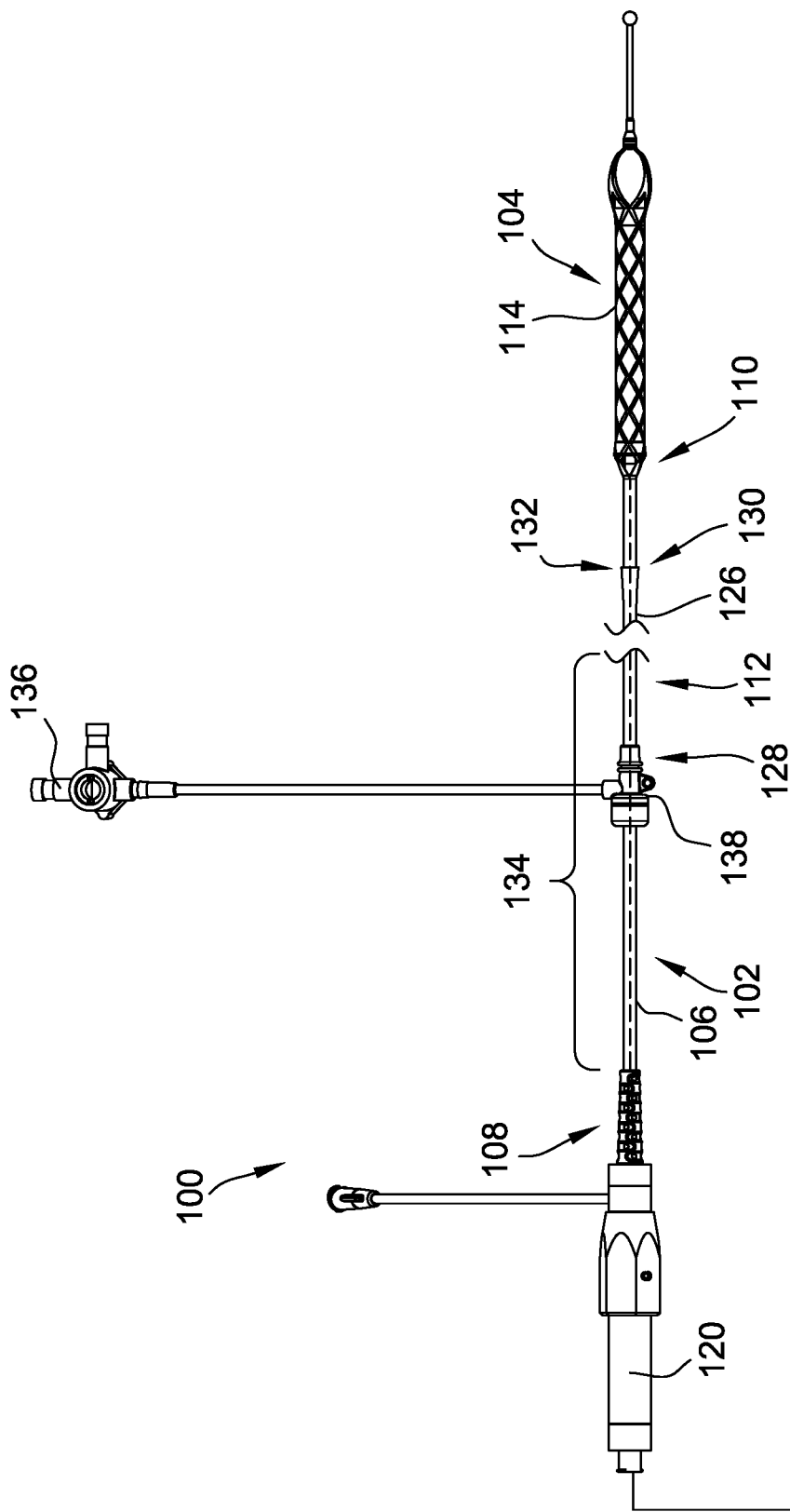
FIG. 1 is a plan view of a catheter system.
Figure 2:
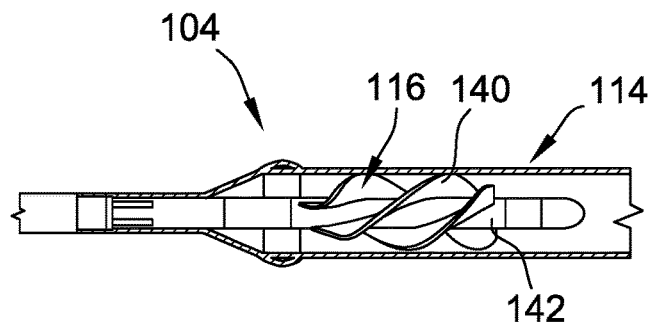
FIG. 2 is an enlarged sectional view of an expandable medical device of the catheter system shown in FIG. 1.
Figure 3:
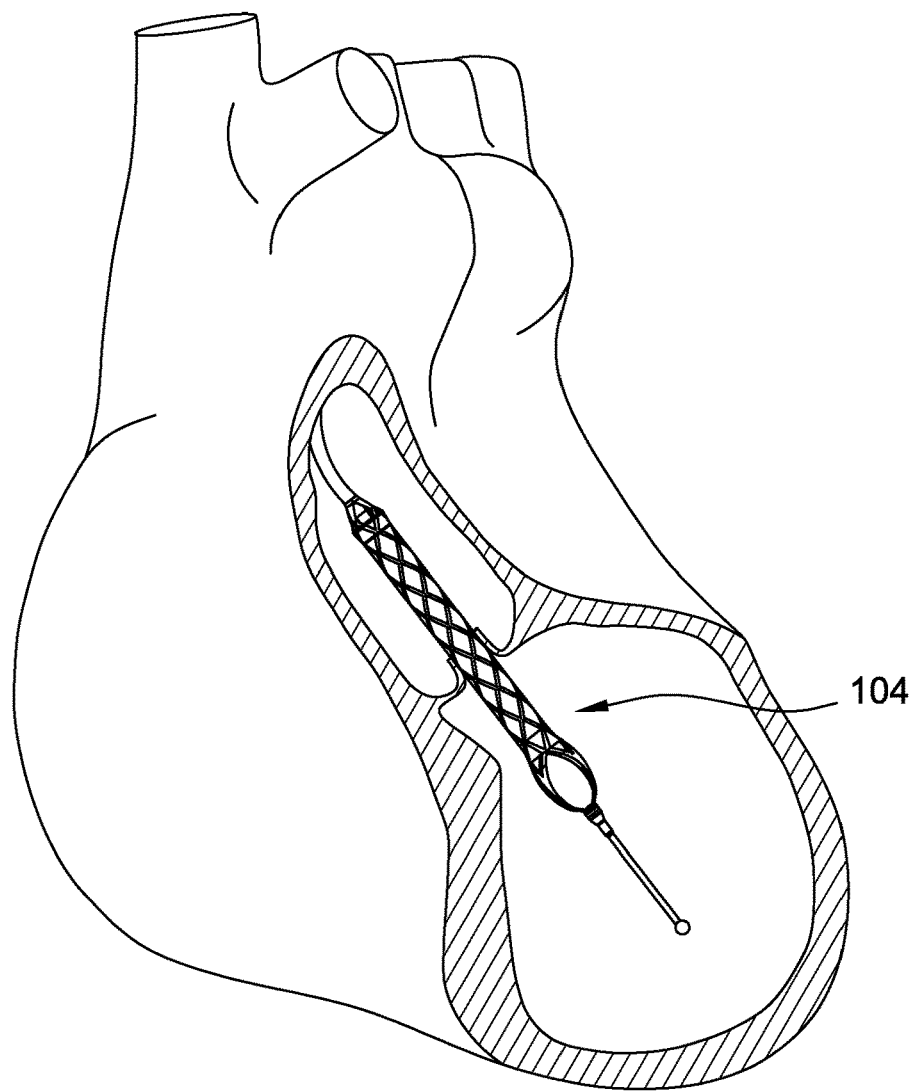
FIG. 3 illustrates one exemplary use of the catheter system shown in FIG. 1 within the chamber of a patient's heart.

The introducer sheath assemblies of the present disclosure are suitable for use in combination with numerous different catheters and catheter systems. FIGS. 1-3 illustrate one non-limiting example of a catheter system 100 in which the introducer sheath assemblies of the present disclosure may be used. In this embodiment, the catheter system 100 is a percutaneous heart pump catheter suitable for providing high performance flow rates of blood within the left ventricle of a patient. While the introducer sheath assemblies of the present disclosure are described with reference to a catheter pump, it should be understood that the disclosed introducer sheath assemblies are not limited to use with a catheter pump and may be used in combination with other catheters and catheter systems. Moreover, it should be understood that the disclosed introducer sheath assemblies are not limited to use with catheters, and may be used in combination with other surgical or medical devices, for example, to facilitate insertion, placement, and/or removal of such surgical and medical devices within a patient's body.

FIG. 1 is a plan view of the catheter system 100. As shown in FIG. 1, the catheter system 100 generally includes a catheter 102 and an expandable medical device 104. The catheter 102 has an elongate body 106 extending from a proximal end 108 to a distal end 110, and includes a retainer sheath 112 disposed over the elongate body 106. As used herein, "proximal" refers to a direction away from the body of a patient and toward an operator of the catheter system 100. In contrast, "distal" as used herein refers to a direction toward the body of a patient and away from the operator. The expandable medical device 104 is coupled at the distal end 110 of the catheter body 106. As used herein, the term "expandable medical device" refers to a catheter medical device, typically coupled to the distal end of the catheter, that is radially expandable from a stored or delivery profile to a deployed or operational profile that is larger than the delivery profile. In this embodiment, the expandable medical device 104 is shown as a radially-expandable heart pump that includes a collapsible and expandable cannula 114 and a collapsible and expandable impeller 116 (shown in FIG. 2). It should be understood that the introducer sheath assemblies of the present disclosure are not limited to use with radially-expandable pumps, and are suitable for use with other types of expandable medical devices. In the collapsed state, the distal end of the catheter system 100 can be advanced to the heart, for example, through an artery. In the expanded state (shown in FIGS. 1-3), the medical device 104 is operational and is capable of performing one more functions for which it is designed. In the illustrated embodiment, the medical device 104 is able to pump or output blood at high flow rates in the expanded state.

In the illustrated embodiment, the catheter system 100 is coupled with a motor 118 for driving the impeller 116. The catheter system 100 includes a coupling 120 that can be engaged with the motor 118 in certain embodiments. In various embodiments, the impeller 116 is rotated by the motor 118 via a drive cable or shaft 122 of the catheter 102 (shown in FIG. 5) when the pump is operating. For example, the motor 118 can be disposed outside the patient. In some embodiments, the motor 118 is coupled to a controller 124 that directs operation of the motor and other components of the catheter system 100 (e.g., an infusion system). In some embodiments, the motor 118 is separate from the controller 124, e.g., to be placed closer to the patient. In other embodiments, the motor 118 is part of the controller 124. In still other embodiments, the motor is miniaturized to be insertable into the patient. In still other embodiments, the catheter system 100 may not include a motor 118.

The retainer sheath 112 is disposed over the catheter body 106, and includes an elongate body 126 that extends from a proximal end 128 to a distal end 130. The retainer sheath elongate body 126 is sized and shaped to receive the catheter body 106 therein to allow the catheter body 106 to be advanced through a lumen defined by the retainer sheath 112.

The retainer sheath 112 is configured to maintain the expandable medical device 104 in the collapsed state to facilitate advancing the catheter 102 through a patient's vasculature. More specifically, the retainer sheath 112 includes a retention section 132 located at the distal end 130 of the retainer sheath elongate body 126 that is disposed over the expandable medical device 104 when in the collapsed state. The retention section 132 thereby enables the expandable medical device 104 to be maintained in the collapsed state until the catheter body distal end 110 is advanced to a desired position, for example, within a patient's heart. In some embodiments, the expandable medical device 104 is configured to self-deploy or self-expand into a deployed or expanded configuration when the expandable medical device 104 is advanced distally out of the retainer sheath 112. The expandable medical device 104 can be collapsed into the collapsed state by advancing the retainer sheath distal end 130 distally over the expandable medical device 104 to cause the expandable medical device 104 to collapse.

In some embodiments, the catheter 102 includes a reduced-diameter proximal portion or section 134 that has a smaller diameter than the distal end of the catheter 102. In the illustrated embodiment, for example, the retention section 132 of the retainer sheath 112 has a suitable diameter for receiving and retaining the expandable medical device 104 therein. The expandable medical device 104, even in the collapsed state, may have a diameter larger than the remainder of the catheter body 106. That is, the catheter body distal end 110 and the expandable medical device 104, in the collapsed state, may have a larger diameter than a proximal section of the catheter 102 that extends from the catheter body proximal end 108. Accordingly, in some embodiments, such as the embodiment shown in FIG. 1, a proximal section 134 of the catheter 102 located at the proximal end 108 may have a reduced diameter relative to the distal end of the catheter 102. In some embodiments, for example, each of the catheter body 106 and the retainer sheath 112 has a reduced diameter along the catheter proximal section 134 relative to the distal ends of the catheter body 106 and the retainer sheath 112. In embodiments that do not have a retainer sheath 112, only the catheter body 106 may have a reduced diameter along the catheter proximal section 134. The reduced-diameter proximal section 134 can have a diameter that is less than 95% of the diameter at the distal end of the catheter 102 (e.g., the diameter of the catheter body distal end 110 and/or the expandable medical device 104, in the collapsed state), less than 90% of the diameter at the distal end of the catheter 102, less than 85% of the diameter at the distal end of the catheter 102, less than 80% of the diameter at the distal end of the catheter 102, less than 75% of the diameter at the distal end of the catheter 102, less than 70% of the diameter at the distal end of the catheter 102, less than 60% of the diameter at the distal end of the catheter 102, and even less than 50% of the diameter at the distal end of the catheter 102. In some embodiments, for example, the distal end of the catheter 102 (i.e., the catheter body distal end 110 and/or the expandable medical device 104, in the collapsed state) has a diameter of between 13-16 French (Fr), and the reduced-diameter proximal section 134 has a diameter of between 9-12 Fr. Reducing the diameter of the catheter proximal section 134 facilitates lowering the profile of the portion of the catheter 102 in the body, and opens up space in the vasculature for blood flow around the remainder of the catheter system 100 that remains in the vasculature after the larger-diameter catheter distal end 110 and expandable medical device 104 are advanced therethrough.

In some embodiments, such as the embodiment illustrated in FIG. 1, a luer 136 or other suitable connector is connected in fluid communication with the proximal end 128 of the retainer sheath 112. In the illustrated embodiment, the luer 136 is connected to the proximal end 128 of the retainer sheath 112 by a hemostatic valve 138 configured to control fluid flow therethrough. The luer 136 can be configured to deliver fluids to the retainer sheath 112, such as priming fluid, infusant, or any other suitable fluid.

With additional reference to FIG. 2, the expandable medical device 104 of the illustrated embodiment is a pump that includes a cannula 114 and an impeller 116. The cannula 114 has a stored, or compressed configuration, and a deployed or expanded configuration. The cannula 114 can be formed of a superelastic material, and in some embodiments, may have various shape memory material properties. The impeller 116 is positioned within the cannula 114, and includes one or more blades 140 that extend from an impeller hub 142. In some embodiments, the blades 140 of the impeller 116 are self-expandable such that when the impeller 116 is positioned at a desired location, e.g., a chamber of a subject's heart, the blades 140 can be expanded into a deployed or expanded configuration, in which the blades 140 extend radially from the hub 142.

The cannula 114 and the impeller 116 may deploy from the stored configurations from within the retainer sheath 112 into the expanded configuration. In such implementations, the retainer sheath 112 can keep the blades 140 and the cannula 114 compressed until the blades 140 and cannula 114 are urged from within a lumen of the retainer sheath 112. Once the blades 140 are released from the sheath assembly, the blades 140 can self-expand to a deployed configuration using strain energy stored in the blades 140 due to deformation of the blades 140 within the retainer sheath 112. The expandable cannula 114 may also self-deploy using stored strain energy after being urged from the retainer sheath 112. The combined energy stored in the expandable cannula 114 and blades 140 generates a force that preferably is opposed by the retention section 132 of the retainer sheath 112. Thus, the retention section 132 should be of robust design to avoid premature deployment of the cannula 114 and blades 140, e.g., prior to positioning in the heart or other source of blood.

In the stored configuration, the expandable medical device 104 has a diameter that is preferably small enough to be inserted percutaneously into a patient's vascular system. Thus, it can be advantageous to fold the expandable medical device 104 into a small enough stored configuration such that the expandable medical device 104 can fit within the patient's veins or arteries, particularly small veins or arteries that are peripheral and superficial, e.g., femoral veins or arteries, jugular and subclavian veins, radial and subclavian arteries. In some embodiments, therefore, the expandable medical device 104 can have a diameter in the stored configuration corresponding to a catheter size between 8 Fr and 21 Fr.

When the expandable medical device 104 is positioned within a chamber of the heart, it can be advantageous to expand the expandable medical device 104 to have a diameter as large as possible in the expanded or deployed configuration. For example, in the illustrated embodiment, an increased diameter of the impeller 116 advantageously increases flow rate through the pump at a given rotational speed. A larger diameter impeller can also lead to an improved ratio of flow rate to hemolysis rate. In some implementations, the expandable medical device 104 can have a diameter corresponding to a catheter size greater than 12 Fr in the deployed configuration. In other embodiments, the expandable medical device 104 can have a diameter corresponding to a catheter size greater than 21 Fr in the deployed or expanded configuration.

FIG. 3 illustrates one exemplary use of the catheter system 100. In the illustrated embodiment, a distal portion of the catheter system 100, which includes the expandable medical device 104, is placed in the left ventricle (LV) of the heart to pump blood from the LV into the aorta. The catheter system 100 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the catheter system 100 in the heart is by percutaneous access and delivery using the Seldinger technique or other methods familiar to cardiologists. These approaches enable the catheter system 100 to be used in emergency medicine, a catheter lab and in other non-surgical settings.

Various additional aspects of the catheter system and associated components may be similar to those disclosed in U.S. Pat. Nos. 7,022,100; 7,393,181; 7,841,976; 7,998,054; 8,376,707; 8,485,961; 8,535,211; 8,591,393; 8,597,170; 8,721,517; 9,138,518; 9,358,329; 9,421,311; 9,446,179; 9,872,947; and 10,105,475, the entire contents of which are incorporated herein for all purposes by reference.

Figure 4:
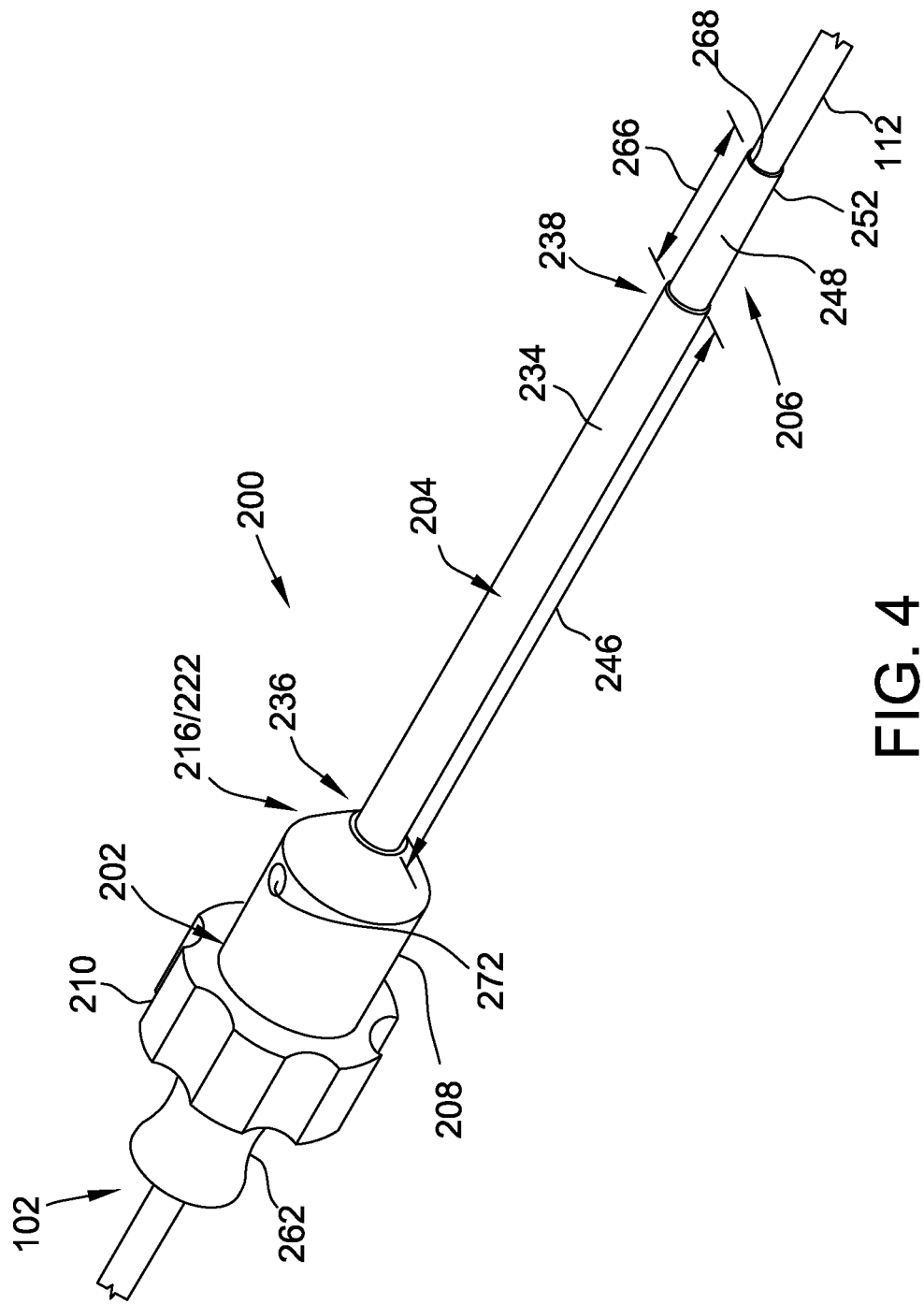
FIG. 4 is a perspective view of one exemplary embodiment of an introducer sheath assembly suitable for use with the catheter system of FIG. 1.

FIG. 4 is a perspective view of one exemplary embodiment of an introducer sheath assembly 200 suitable for use with a catheter system including, but not limited to, the catheter system 100 shown and described above with reference to FIGS. 1-3. As described further herein, the introducer sheath assembly 200 facilitates reducing obstructions within a patient's vasculature during catheter medical procedures by permitting an initial introducer sheath (also referred to herein as a "first introducer sheath") to be removed from the patient's vasculature, such that a relatively small diameter portion of the catheter remains in the patient's vasculature. More specifically, in at least some known medical procedures, a relatively long first introducer sheath is initially inserted into a patient's blood vessel through an incision site to facilitate advancing a catheter to a desired location within a patient, for example, a chamber of the patient's heart. The first introducer sheath is typically sized to permit a large diameter distal portion of the catheter to pass therethrough. The introducer sheath assembly 200 is configured to seal the incision site through which the first introducer sheath is inserted such that the first introducer sheath can be removed from the patient's vasculature, for example, once the distal end of catheter system is advanced to a desired location. The introducer sheath assembly thereby permits a relatively small diameter portion of the catheter system (e.g., a reduced diameter proximal portion of the catheter 102) to remain in the patient's vasculature, thereby reducing obstruction to blood flow. Moreover, as described in more detail herein, the introducer sheath assembly 200 is configured to fill a gap between the introducer sheath assembly 200 and the relatively-small diameter portion of the catheter that remains in the patient's vasculature following removal of the first introducer sheath, while still permitting the relatively-large diameter distal end of the catheter to be removed through the introducer sheath assembly.

As shown in FIG. 4, the introducer sheath assembly 200 includes a valve 202, an introducer sheath 204 connected to and protruding from the valve 202, and a tubular plug 206 that is releasably fixed relative to the introducer sheath 204 such that the plug can be removed or withdrawn from the introducer sheath 204, as described in greater detail herein. In this embodiment, the introducer sheath 204 and the tubular plug 206 are coupled to the valve 202 such that the introducer sheath assembly 200 is movable as a unit along the catheter body 106 and/or the retainer sheath 112. With additional reference to FIG. 5, the introducer sheath assembly 200 is disposed on the catheter 102, specifically, on the retainer sheath 112 and the catheter body 106. In the illustrated embodiment, the introducer sheath assembly 200 is disposed on a proximal end of the catheter 102, specifically, along the reduced-diameter proximal section 134 of the catheter 102. In some embodiments, the introducer sheath assembly 200 is disposed on the catheter 102 distally from the fluid valve 138 (shown in FIG. 1). In other embodiments, the fluid valve 138 may be incorporated with the introducer sheath assembly 200, for example, as the valve 202.

The valve 202 is configured to control fluid flow through one or more lumens defined by the introducer sheath assembly 200 and/or the catheter 102, for example, to inhibit blood flow out of a patient. The valve 202 includes a valve body 208, an actuator 210, and a valve member 212. The valve 202 has a proximal end 214 and a distal end 216, and has an elongate passage 218 defined therein. In this embodiment, the elongate passage 218 is defined by and extends through each of the valve body 208, the actuator 210, and the valve member 212. The valve body 208 has a proximal end 220 and a distal end 222, which in this embodiment, defines the distal end 216 of the valve 202. The actuator 210 is coupled to the valve body proximal end 220, and the valve member 212 is positioned between the valve body 208 and the actuator 210.

In this embodiment, the valve 202 is a rotatable hemostatic valve that includes a rotatable actuator 210 and a compressible valve member 212. More specifically, the actuator 210 is configured to compress the valve member 212 between an engagement portion 224 of the actuator 210 and the valve body 208, and thereby cause the valve member 212 to deflect radially inward and apply a radial compressive force on the plug 206, as indicated by arrows 226 in FIG. 6. The valve member 212 thereby seals one or more lumens defined between the plug 206 and the catheter 102 and/or defined within the catheter 102. The actuator 210 is threadably coupled to the valve body 208 in this embodiment such that rotation of the actuator 210 in a first direction (e.g., clockwise) displaces the actuator 210 towards the valve member 212, as indicated by arrows 228 in FIG. 6, and compresses the valve member 212 between the actuator 210 and the valve body 208. Rotation of the actuator 210 in a second, opposite direction (e.g., counterclockwise) displaces the actuator 210 away from the valve member 212, releasing compression on the valve member 212. It should be understood that the introducer sheath assembly 200 may include any suitable valve that enables the introducer sheath assembly 200 to function as described herein, and is not limited to rotatable hemostatic valves.

The valve 202 also includes a retainer 230 for releasably fixing the plug 206 relative to the introducer sheath 204. In this embodiment, the retainer 230 includes an O-ring that is positioned within an annular recess 232 defined by the actuator 210. The O-ring engages a portion of the plug 206, and maintains an axial position of the plug 206 relative to the introducer sheath 204 via a friction fit. In other embodiments, the valve 202 may include a retainer other than an O-ring for releasably fixing the plug 206 relative to the introducer sheath 204. In yet other embodiments, one or both of the plug 206 and the introducer sheath 204 may include a retainer for maintaining a fixed relative position of the two components.

The introducer sheath 204 includes an elongate body 234 extending from a proximal end 236 to a distal end 238, and defines a lumen 240 therein that extends from the introducer sheath proximal end 236 to the introducer sheath distal end 238. The introducer sheath body 234 has an outer diameter 242 that is sized and shaped to seal an incision formed, for example, in a patient's vasculature. The introducer sheath body 234 may have any suitable outer diameter 242 that enables the introducer sheath assembly 200 to function as described herein. In some embodiments, the outer diameter 242 of the introducer sheath 204 is the same as the initial or first introducer sheath used to introduce the catheter 102 into a patient's vasculature. Suitable outer diameters 242 of the introducer sheath body 234 include, for example and without limitation, between 8 Fr and 21 Fr, between 8 Fr and 19 Fr, between 10 Fr and 21 Fr, between 8 Fr and 17 Fr, between 10 Fr and 19 Fr, between 12 Fr and 21 Fr, between 8 Fr and 15 Fr, between 10 Fr and 17 Fr, between 12 Fr and 19 Fr, between 14 Fr and 21 Fr, between 10 Fr and 15 Fr, between 12 Fr and 17 Fr, and between 14 Fr and 19 Fr. In some embodiments, the outer diameter 242 of the introducer sheath body 234 is less than 8 Fr. In yet other embodiments, the outer diameter 242 of the introducer sheath 204 is greater than 21 Fr. In one embodiment, the outer diameter 242 of the introducer sheath body 234 is 14 Fr.

The introducer sheath lumen 240 is configured to be slidably disposed over the catheter 102 (e.g., over the retainer sheath 112 and/or the catheter body 106) such that the catheter 102 can be advanced distally and proximally relative to the introducer sheath 204. The introducer sheath lumen 240 is sized to permit the expandable medical device 104 and retainer sheath retention section 132 to fit therethrough. In some embodiments, for example, the introducer sheath 204 has an inner diameter 244 sized larger than an outer diameter of the expandable medical device 104 in the collapsed state and/or an outer diameter of the retainer sheath retention section 132. In such embodiments, the introducer sheath 204 may be used to re-sheath or collapse the expandable medical device 104 when removing the catheter 102 from a patient, for example, when the expandable medical device 104 cannot be re-sheathed or collapsed with the retainer sheath 112. In some embodiments, the introducer sheath inner diameter 244 is sized to permit an object having an outer diameter of up to 13 Fr, up to 14 Fr, up to 15 Fr, and even up to 16 Fr to pass through the introducer sheath lumen 240.

In this embodiment, the introducer sheath 204 is coupled to the valve body 208 at the valve body distal end 222. The introducer sheath 204 may be coupled to the valve body 208 using any suitable fastening means including, for example and without limitation, a frictional fit, adhesives, and tacking. The introducer sheath 204 extends from the valve body distal end 222 by a length 246 (FIG. 4). The introducer sheath 204 may extend from the valve body 208 by any suitable length 246 that enables the introducer sheath assembly 200 to function as described herein including, for example and without limitation, between 2 centimeters (cm) and 12 cm, between 2 cm and 10 cm, between 4 cm and 12 cm, between 2 cm and 8 cm, between 4 cm and 10 cm, between 6 cm and 12 cm, between 2 cm and 6 cm, between 4 cm and 8 cm, between 6 cm and 10 cm, between 8 cm and 12 cm, between 4 cm and 6 cm, between 6 cm and 8 cm, and between 8 cm and 10 cm. The length 246 the introducer sheath 204 extends from the valve body 208 is suitably less than the initial or first introducer sheath used to introduce the catheter system 100 into the vasculature of a patient. In some embodiments, for example, the length 246 the introducer sheath 204 extends from the valve body 208 is less than one-half a length of the initial introducer sheath, and even less than one-third the length of the initial introducer sheath.

The introducer sheath 204 may be constructed of any suitable materials using any suitable techniques that enable the plug introducer sheath 204 to function as described herein. In some embodiments, the introducer sheath 204 has a suitably rigid construction to enable to the introducer sheath 204 to re-sheath or collapse the expandable medical device 104 when the catheter 102 is removed from a patient. Suitable constructions for the introducer sheath 204 include, for example and without limitation, a braided reinforced sheath (e.g., braided nitinol) with a lubricious liner, and a thicker-wall single material component.

The plug 206 is disposed along the catheter 102, between the introducer sheath 204 and the catheter 102. The plug includes an elongate body 248 extending from a proximal end 250 (FIG. 5) to a distal end 252 of the plug 206, and defines a lumen 254 extending therethrough. The elongate body 248 extends through each of the elongate passage 218 and the introducer sheath lumen 240.

Figure 5:
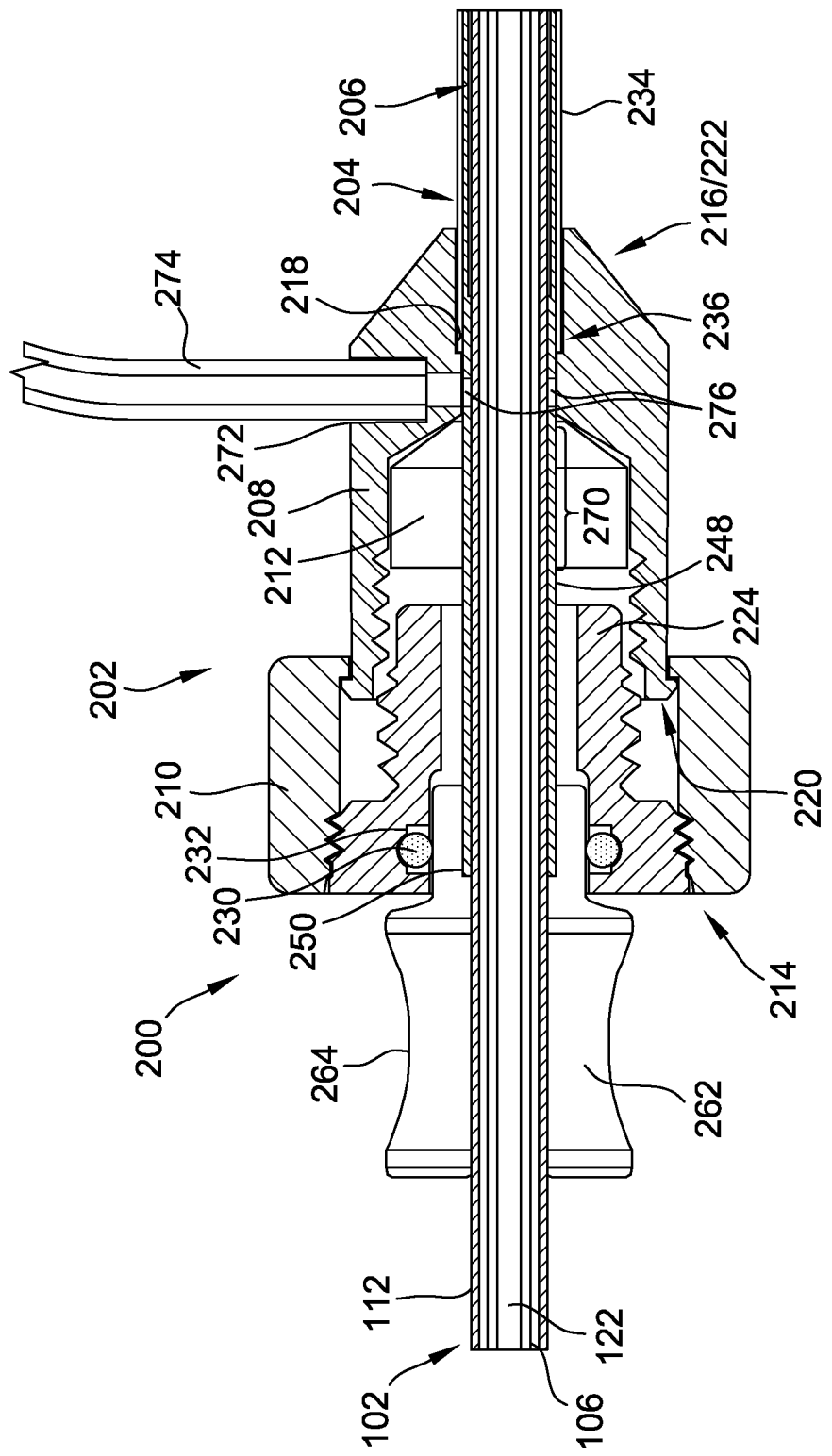
FIG. 5 is a sectional view of the introducer sheath assembly of FIG. 4.
Figure 6:
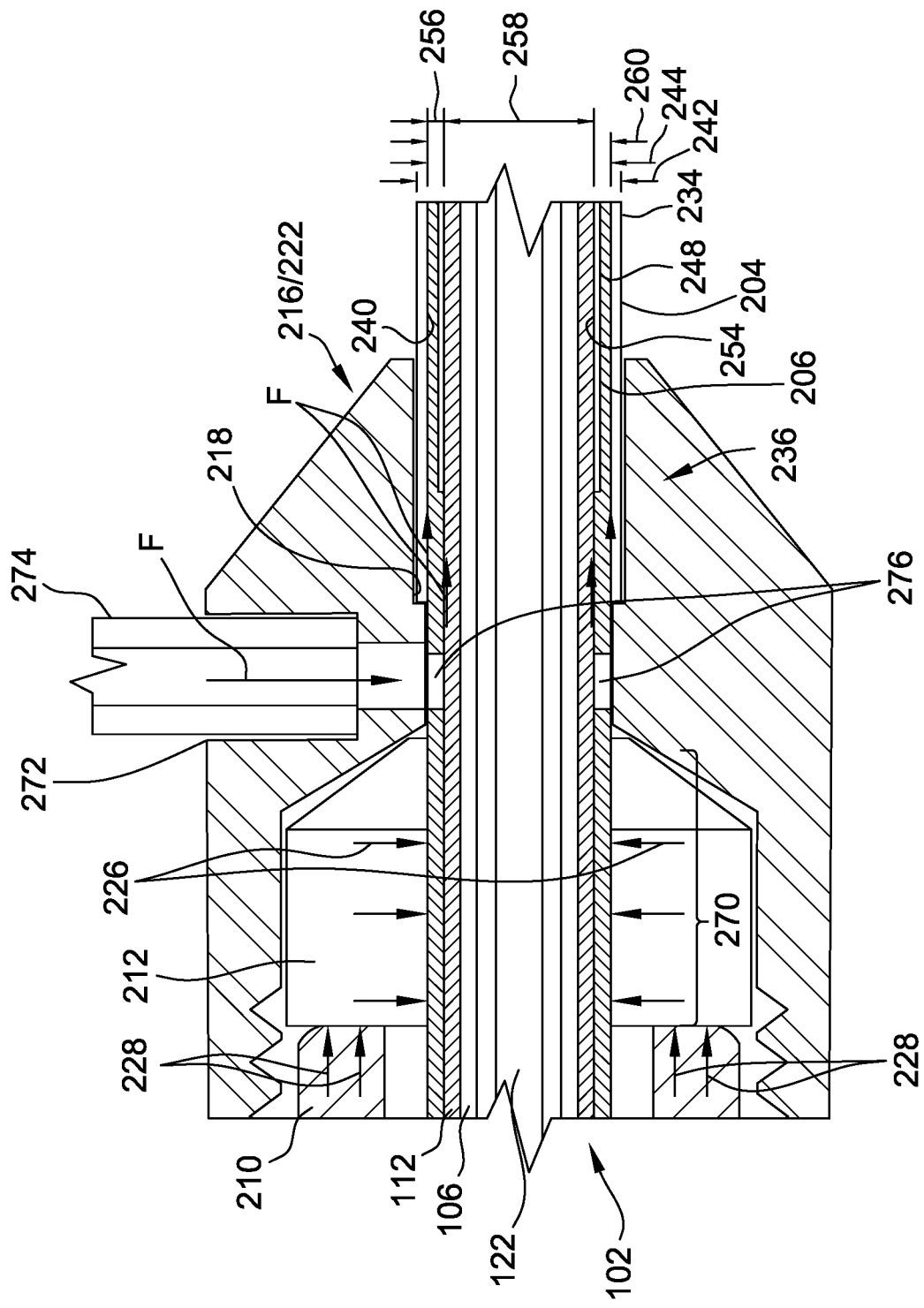
FIG. 6 is an enlarged sectional view of the introducer sheath assembly of FIG. 4.

In some embodiments, such as the embodiment illustrated in FIGS. 4-6, the introducer sheath assembly 200 is disposed over the reduced-diameter proximal section 134 of the catheter 102 such that a gap 256 is defined between the introducer sheath 204 and the catheter 102 (e.g., the retainer sheath 112). As shown in FIG. 6, the plug 206 is disposed over the catheter 102 (specifically, over the catheter body 106 and the retainer sheath 112 in this embodiment), and between the catheter 102 and the introducer sheath 204 to occlude the gap 256 defined therebetween. The plug 206 has a suitable thickness to substantially fill or occlude the gap 256 and inhibit outward fluid flow (i.e., towards a proximal end of the introducer sheath assembly 200) therethrough. That is, in some embodiments, the plug body 248 has a suitable inner diameter 258 and outer diameter 260 to substantially fill the gap 256 between the introducer sheath 204 and the catheter 102. In some embodiments, for example, the plug body 248 has an outer diameter 260 of between 85% and 100% of the introducer sheath inner diameter 244, between 85% and 95% of the introducer sheath inner diameter 244, or between 90% and 100% of the introducer sheath inner diameter 244. Further, in some embodiments, the plug body 248 has an inner diameter 258 of between 1.0 and 1.25 times an outer diameter of the catheter 102 (e.g., the reduced-diameter proximal section of the catheter 102), between 1.0 and 1.2 times an outer diameter of the catheter 102, or between 1.0 and 1.15 times an outer diameter of the catheter 102. In one particular embodiment, the plug body 248 has an outer diameter 260 of 13 Fr, and inner diameter 258 sized to permit an object having a diameter up to 10 Fr to pass therethrough.

As noted above, the plug 206 is releasably fixed relative to the introducer sheath 204 such that the plug 206 can be removed from the introducer sheath lumen 240, for example, to allow a relatively-large diameter distal end of the catheter 102 (e.g., the expandable medical device 104 and/or the retainer sheath retention section 132) to pass therethrough. In the illustrated embodiment, the plug 206 is releasably coupled to the valve 202, specifically, to the valve actuator 210 by an O-ring. In one method of using the introducer sheath assembly 200, the plug 206 is removed from the introducer sheath lumen 240 by pulling the plug 206 proximally relative to the introducer sheath 204, thereby decoupling the plug 206 from the valve 202, prior to the catheter 102 being removed from a patient's vasculature.

In the illustrated embodiment, the plug 206 includes a handle 262 coupled with the plug proximal end 250 to facilitate positioning and/or moving the plug 206 relative to the introducer sheath 204 and/or the valve 202. The handle 262 has a diameter larger than the plug body outer diameter 260 to facilitate grasping the handle 262. Further, in this embodiment, the handle 262 includes an annular concave groove 264 to facilitate grasping the handle 262. The handle 262 may include other gripping features in addition to or as an alternative to the concave groove, including, for example and without limitations, ribs, grooves, and textured surface(s). The handle 262 extends proximally from the valve proximal end 214, and is accessible from an exterior of the valve 202. The plug handle 262 may be formed integrally with the plug body 248 (i.e., as a unitary member), or may be formed separately from the plug body 248 and coupled thereto. In the illustrated embodiment, the plug 206 is fixed relative to the introducer sheath 204 by the plug handle 262 being secured to the O-ring via a frictional fit.

Referring again to FIG. 4, the plug distal end 252 protrudes from the distal end 238 of the introducer sheath 204 by a distance 266. The plug distal end 252 may protrude from the introducer sheath distal end 238 by any suitable distance 266 that enables the introducer sheath assembly 200 to function as described herein. In some embodiments, for example, the plug distal end 252 protrudes from the introducer sheath distal end 238 by a distance 266 of up to 1 cm, up to 2 cm, up to 3 cm, 4 cm, up to 5 cm, up to 6 cm, up to 7 cm, up to 8 cm, and even up to 10 cm.

In some embodiments, the plug distal end 252 tapers radially inward towards a distal tip 268 of the plug 206 to facilitate insertion of the plug distal end 252 into an incision site. Moreover, in some embodiments, the plug body 248 includes multiple hardness or durometer zones. That is, the plug body 248 may be constructed to have zones of differing hardness or stiffness. In some embodiments, for example, the plug distal end 252 has a relatively stiff or hard construction relative to the remainder of the plug body 248, for example, to facilitate insertion of the plug distal end 252 into an incision site. Additionally or alternatively, in some embodiments, a proximal portion 270 of the plug body 248, such as the portion of the plug body 248 that engages the valve member 212, has a relatively soft, flexible, or elastic construction relative to the remainder of the plug body 248, for example, to facilitate compression by the valve member 212 and sealing of one or more lumens defined by the plug body 248 and/or the catheter 102. That is, the proximal portion 270 of the plug body 248 may be radially compliant to facilitate sealing the lumens defined by or within the plug 206.

The plug 206 may be constructed of any suitable materials using any suitable techniques that enable the plug 206 to function as described herein. In one embodiment, the plug 206 is formed by an extrusion process, and multiple hardness zones are formed along the plug body 248 using known reflow techniques. Suitable materials from which the plug 206 may be constructed include, for example and without limitation, polyethylene.

Referring to FIGS. 5-6, the valve body 208 defines a fluid port 272 that is in fluid communication with the valve body elongate passage 218. The fluid port 272 is configured for connection to a fluid source (e.g., heparinized saline) via a fluid line 274, and allows one or more fluids F to be delivered or supplied to one or more lumens defined by the introducer sheath 204 and/or the plug 206. In some embodiments, fluid is supplied to one or more lumens defined by the introducer sheath 204 and/or the plug 206 to flush the lumens and inhibit blood products from accumulating and forming clots within the introducer sheath assembly 200. In this embodiment, the fluid port 272 is located between the valve member 212 and the distal end 222 of the valve body 208, and extends radially inward from a radial outer surface of the valve body 208 to the elongate passage 218.

The introducer sheath proximal end 236 is positioned distally from the valve body fluid port 272 such that the introducer sheath lumen 240 is in fluid communication with the fluid port 272. Additionally, in this embodiment, the plug 206 defines one or more fluid ports 276 that extend through the plug body 248. When the plug 206 is connected to the valve 202, as shown in FIGS. 4-6, the plug fluid ports 276 are aligned with and coupled in fluid communication with the valve body fluid port 272 such that fluid may be supplied to the plug lumen 254 via the valve body fluid port 272. In other words, the plug fluid ports 276 enable fluid to be supplied to the plug lumen 254 using the same fluid port 272 used to supply fluid to the introducer sheath lumen 240. In this embodiment, the plug fluid ports 276 are located distally from the elastic proximal portion 270 of the plug body 248 that engages the valve member 212 to inhibit fluid supplied through the fluid port 272 from leaking out of the proximal end of the introducer sheath assembly 200.

Figure 7:
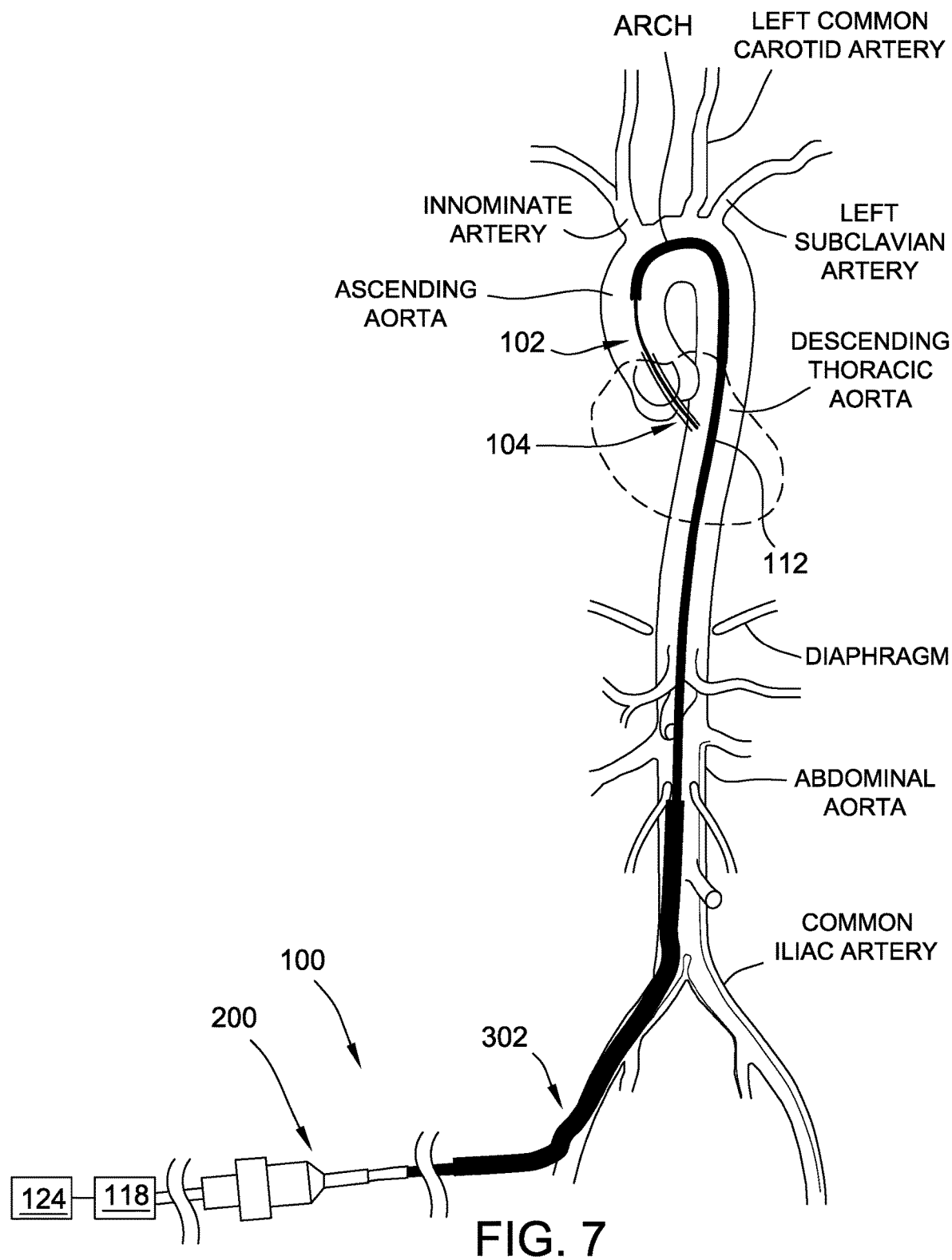
FIG. 7 is a simplified diagram of a patient's vasculature illustrating one technique for introducing the catheter system of FIG. 1 using an initial or first introducer sheath.

FIG. 7 is a simplified diagram of a patient's vasculature illustrating one technique for introducing the catheter system 100 using an initial or first introducer sheath 302. The catheter system 100 is shown in FIG. 7 in one operational configuration, following insertion of the catheter 102 into the patient's vasculature through an incision site using the first introducer sheath 302. More specifically, FIG. 7 shows the retainer sheath 112 in a proximal position, with the expandable medical device 104 advanced distally out of the retainer sheath 112 and in the expanded state. In FIG. 7, the catheter system 100 is illustrated with the first introducer sheath 302 positioned within the patient's vasculature. As described herein, the introducer sheath assemblies of the present disclosure enable the first introducer sheath 302 to be removed from the patient's vasculature, and thereby facilitate reducing obstructions to blood flow within the patient's vasculature. In some embodiments, for example, the introducer sheath assembly 200 is disposed on a proximal section of the catheter 102, as shown in FIG. 7. Once the distal end of the catheter 102 is advanced to a desired location within the patient, the initial introducer sheath 302 is removed from the patient's vasculature, and removed from the catheter 102, for example, by peeling the first introducer sheath 302 off of the catheter 102.

Figure 8:
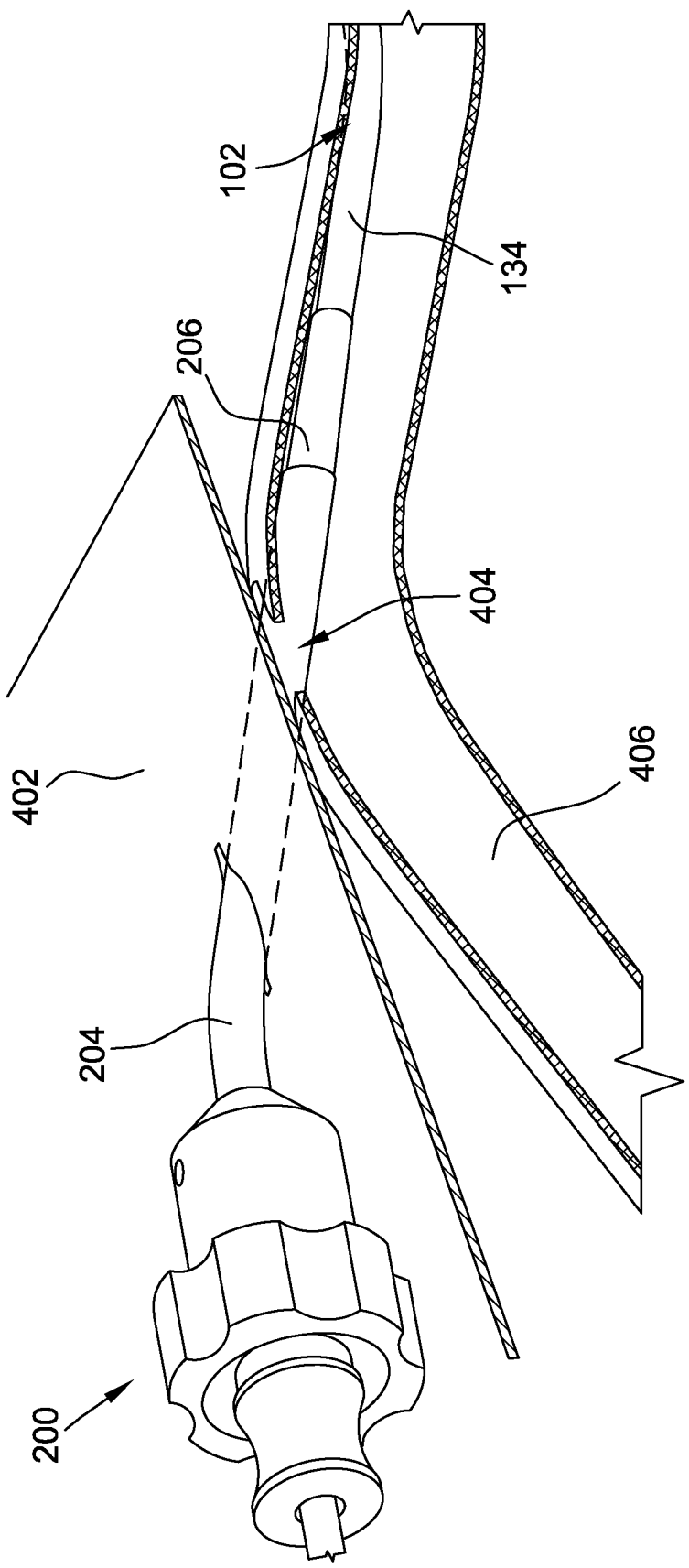
FIG. 8 is a perspective view of the introducer sheath assembly of FIG. 4 disposed in a patient's vasculature.

With additional reference to FIG. 8, the introducer sheath assembly 200 is subsequently advanced along the catheter 102 and through the patient's skin 402 to the incision site 404 formed in the patient's vessel 406 to fill the opening at the incision site 404. The removable plug 206 of the introducer sheath assembly substantially fills or occludes the gap formed between the introducer sheath 204 and the catheter 102, such that the proximal portion of the catheter 102 can have a reduced diameter relative to the distal end. This facilitates reducing the size of the catheter 102 positioned within the patient's vasculature, as shown in FIG. 8, thereby reducing obstructions to blood flow. When the catheter 102 is to be removed from the patient, the plug 206 can be removed from the introducer sheath 204 (e.g., by sliding the plug 206 proximally along the catheter 102), thereby allowing the large diameter distal end of the catheter to pass through the introducer sheath lumen 240. Once the catheter 102 is removed from the introducer sheath 204, the valve 202 may be actuated to close valve member 212 (e.g., by rotating the actuator 210 and causing the valve member 212 to compress the introducer sheath 204) to inhibit blood flow out of the introducer sheath 204. Additionally, in some embodiments, the introducer sheath 204 may be left in place, for example, to allow access for other catheters to be introduced by an operator.

In other embodiments, the introducer sheath assembly 200 can be used to introduce the catheter system 100 into a patient's vasculature (i.e., without the first introducer sheath 302). In some embodiments, for example, the catheter system 100 is initially assembled with the distal tip of the catheter 102 (e.g., the expandable medical device 104) positioned distally from the introducer sheath assembly 200, and the removable plug 206 inserted into the introducer sheath 204 as shown, for example in FIG. 4. In such embodiments, the removable plug 206 can be removed from the introducer sheath 204 (i.e., pulled proximally out of the introducer sheath 204), and the expandable medical device 104 can be pulled proximally toward the introducer sheath 204 such that expandable medical device 104 is stored within the introducer sheath lumen 240 in the collapsed state. The expandable medical device 104 may be retained in the collapsed state within the introducer sheath lumen 240 by the introducer sheath 204, or another component of the catheter system 100, such as the retainer sheath 112. The introducer sheath 204 can then be inserted into a patient's vasculature (e.g., through an incision site or opening formed in a vessel) to introduce the catheter system 100 into the patient's vasculature. The catheter 102, including the expandable medical device 104, can then be advanced distally out of the introducer sheath 204 and to a desired location within the patient. The expandable medical device 104 may be retained in the collapsed state (e.g., by retainer sheath 112) while the expandable medical device 104 is advanced to the desired location within the patient. The removable plug 206 can be advanced distally along the catheter 102 to fill or occlude the gap 256 formed between the introducer sheath 204 and the reduced-diameter proximal section 134 of the catheter 102 until the catheter 102 is to be removed from the patient. To remove the catheter 102 from the patient, the removable plug 206 is first removed from the introducer sheath 204 by pulling the removable plug 206 proximally relative to the introducer sheath 204 to the allow larger diameter distal end of catheter 102 (e.g., catheter body distal end 110 and the expandable medical device 104, in the collapsed state) to pass through the introducer sheath lumen 240. The catheter 102 is subsequently pulled proximally through the introducer sheath 204 to remove the catheter 102 from the patient. The expandable medical device 104 can be re-sheathed or collapsed using the retainer sheath 112, or using the introducer sheath 204, as described above.

Figure 9:
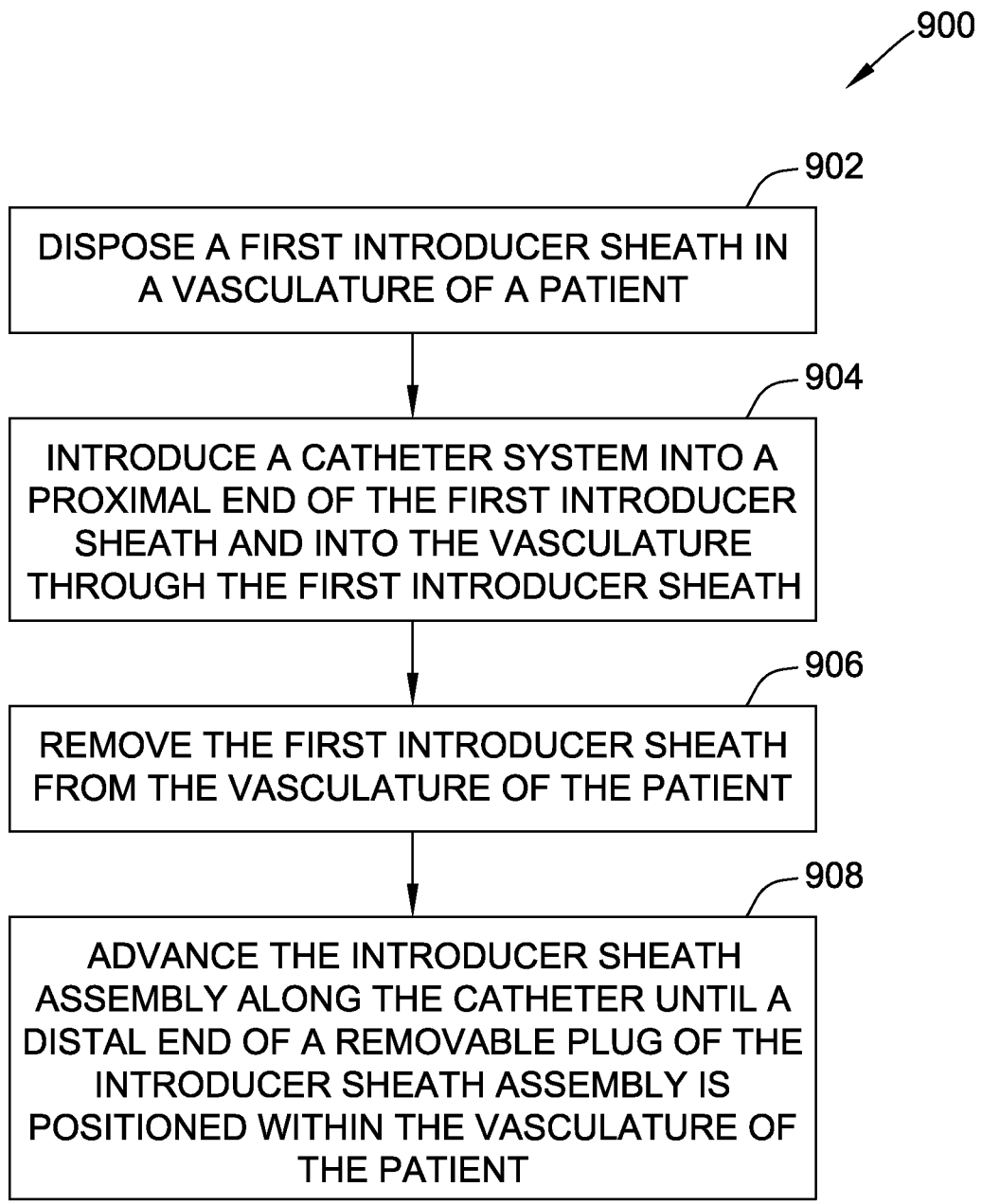
FIG. 9 is a flow diagram illustrating one embodiment of a method for introducing a catheter system into a patient's vasculature.

FIG. 9 is a flow diagram illustrating one exemplary embodiment of a method 900 for introducing a catheter system, such as the catheter system 100, into a patient's vasculature. In the illustrated embodiment, the method 900 includes disposing 902 a first introducer sheath, such as the first introducer sheath 302, in a vasculature of a patient, and introducing 904 a catheter system, such as the catheter system 100, into a proximal end of the first introducer sheath and into the vasculature through the first introducer sheath. The catheter system includes a catheter, such as the catheter 102, having an expandable medical device coupled with a distal end of the catheter, and an introducer sheath assembly, such as the introducer sheath assembly 200, coupled to a proximal end of the catheter. The introducer sheath assembly includes a second introducer sheath, such as the introducer sheath 204, and a removable plug, such as the plug 206, disposed between the second introducer sheath and the catheter. The method 900 further includes removing 906 the first introducer sheath from the vasculature of the patient, and advancing 908 the introducer sheath assembly along the catheter until a distal end of the removable plug is positioned within the vasculature of the patient.

In some embodiments, the catheter includes a reduced-diameter proximal portion that as a smaller diameter than a distal end of the catheter. In such embodiments, advancing 908 the introducer sheath assembly along the catheter may include occluding a gap formed between an incision site in the patient and the reduced-diameter proximal portion of the catheter.

In some embodiments, the method 900 further includes deploying the expandable medical device within the patient such that the expandable medical device radially expands from a collapsed state to an expanded state. In some embodiments, deploying the expandable medical device includes advancing the expandable medical device distally relative to and out of a retainer sheath of the catheter, thereby expanding the expandable medical device.

In some embodiments, the method 900 further includes removing the plug from the second introducer sheath, and removing the catheter from the vasculature of the patient through a lumen defined by the second introducer sheath. In embodiments where the catheter includes a retainer sheath, the method 900 may further include collapsing the expandable medical device with the retainer sheath prior to removing the catheter from the vasculature of the patient. In yet other embodiments, removing the catheter from the vasculature of the patient includes collapsing the expandable medical device with the second introducer sheath by engaging a distal end of the second introducer sheath with the medical device.

Further, in some embodiments, the method 900 further includes coupling a fluid source to a fluid port defined by a valve of the introducer sheath assembly, and supplying fluid to one or more lumens defined by the second introducer sheath and/or the plug. In some embodiments, the method 900 includes supplying fluid to both a lumen defined by the introducer sheath and a lumen defined by the plug via the valve fluid port.

Figure 10:
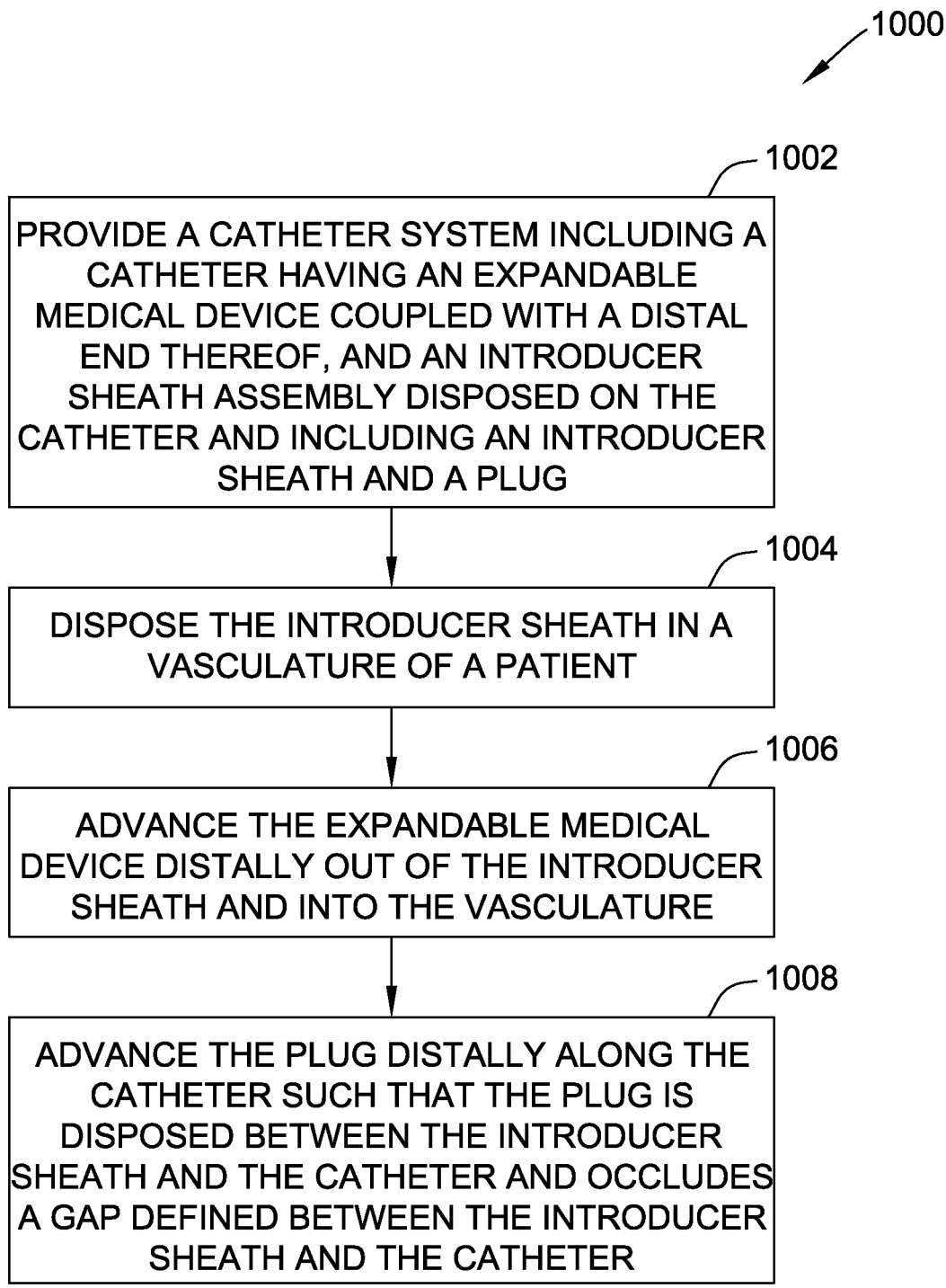
FIG. 10 is a flow diagram illustrating another embodiment of a method for introducing a catheter system into a patient's vasculature.

FIG. 10 is a flow diagram illustrating another exemplary embodiment of a method 1000 for introducing a catheter system, such as the catheter system 100, into a patient's vasculature. In the illustrated embodiment, the method 1000 includes providing 1002 a catheter system, such as the catheter system 100, that includes a catheter, such as catheter 102, including an expandable medical device, such as medical device 104, coupled with a distal end thereof. The catheter system further includes an introducer sheath assembly, such as introducer sheath assembly 200, disposed on the catheter, and includes an introducer sheath, such as introducer sheath 204, and a plug, such as plug 206. The expandable medical device is stored within the introducer sheath in a collapsed state (retained in the collapsed state, for example, by the introducer sheath or a separate retainer sheath, such as retainer sheath 112), and the plug is disposed proximally from the expandable medical device. The method 1000 further includes disposing 1004 the introducer sheath in a vasculature of a patient, and advancing 1006 the expandable medical device distally out of the introducer sheath and into the vasculature. The expandable medical device may be retained in the collapsed state (e.g., using a retainer sheath, such as retainer sheath 112) until the expandable medical device is advanced to a desired location within a patient's vasculature. The method 1000 further includes advancing 1008 the plug distally along the catheter such that the plug is disposed between the introducer sheath and the catheter and occludes a gap defined between the introducer sheath and the catheter.

Although certain steps of the example methods are numbered, such numbering does not indicate that the steps must be performed in the order listed. Thus, particular steps need not be performed in the exact order they are presented, unless the description thereof specifically requires such order. The steps may be performed in the order listed, or in another suitable order.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A catheter system comprising:
a catheter comprising an elongate body having an expandable medical device coupled with a distal end thereof;
an introducer sheath comprising an elongate body defining a lumen therein, the introducer sheath disposed over the catheter to form a gap therebetween; and
a tubular plug comprising an elongate body, the tubular plug extending through the lumen of the introducer sheath, the tubular plug disposed between the catheter and the introducer sheath to occlude the gap, wherein the tubular plug is releasably fixed relative to the introducer sheath such that the tubular plug is remov- able from the lumen to allow the expandable medical device to pass therethrough.

2. The catheter system of claim 1, wherein the catheter further comprises a retainer sheath disposed over the elongate body and having a proximal section and a retention section disposed over the expandable medical device to maintain the expandable medical device in a collapsed state.

3. The catheter system of claim 1, wherein the catheter includes a reduced-diameter proximal portion having a smaller diameter than a distal end of the catheter, and wherein the introducer sheath is disposed along the reduced-diameter proximal portion of the catheter such that the tubular plug occludes the gap formed between the introducer sheath and the reduced-diameter proximal portion of the catheter.

4. The catheter system of claim 1, further comprising a valve comprising a valve body defining an elongate passage therethrough, wherein the introducer sheath protrudes from a distal end of the valve body, and wherein the tubular plug extends through the elongate passage defined by the valve body.

5. The catheter system of claim 4, wherein the valve engages a proximal portion of the tubular plug to seal a lumen defined between the tubular plug and the catheter.

6. The catheter system of claim 4, wherein the valve body comprises a fluid port in fluid communication with the elongate passage, wherein the lumen is in fluid communication with the valve body fluid port, and wherein the tubular comprises a fluid port in fluid communication with the valve body fluid port.

7. The catheter system of claim 4, wherein the valve comprises a rotatable actuator and a compressible valve member, wherein rotation of the rotatable actuator displaces the actuator towards the compressible valve member and compresses the valve member between the rotatable actuator and the valve body causing the valve member to deflect radially inward and apply a radial compressive force on the tubular plug to seal the lumen defined between the tubular plug and the catheter.

8. The catheter system of claim 4, wherein the tubular plug comprises a handle coupled with a proximal end of the tubular plug and extends proximally from the valve.

9. The catheter system of claim 1, wherein a distal end of the tubular plug has a relatively stiff construction as compared to a remainder of the tubular plug.

10. The catheter system of claim 1, wherein a distal end of the tubular plug tapers radially inward towards a distal tip of the tubular plug.

11. The catheter system of claim 1, wherein the expandable medical device comprises:
an expandable cannula; and
an impeller disposed within the expandable cannula and operable to draw fluid into the expandable cannula when rotated in the fluid.

12. An introducer sheath assembly comprising:
a valve comprising a valve body defining an elongate passage therethrough;
an introducer sheath protruding from the valve body distal end, the introducer sheath including an elongate body defining a lumen; and
a tubular plug extending through each of the elongate passage and the lumen of the introducer sheath, wherein a distal end of the tubular plug protrudes from a distal end of the introducer sheath, and wherein the tubular plug is releasably fixed relative to the introducer sheath such that the tubular plug is removable from the lumen.

13. The introducer sheath assembly of claim 12, wherein the valve engages a proximal portion of the tubular plug.

14. The introducer sheath assembly of claim 12, wherein the valve body comprises a fluid port in fluid communication with the elongate passage, wherein the lumen is in fluid communication with the valve body fluid port, and wherein the tubular plug comprises a fluid port in fluid communication with the valve body fluid port.

15. The introducer sheath of claim 12, wherein the valve is operable to apply a radial compressive force on the tubular plug to seal a lumen defined between the plug and a catheter extending therethrough.

16. The introducer sheath assembly of claim 12, wherein the valve comprises a rotatable actuator and a compressible valve member, wherein rotation of the rotatable actuator displaces the actuator towards the compressible valve member and compresses the valve member between the rotatable actuator and the valve body causing the valve member to deflect radially inward and apply the radial compressive force on the tubular plug.

17. The introducer sheath assembly of claim 12, wherein the tubular plug comprises a handle coupled with a proximal end of the tubular plug and extends proximally from the valve.

18. The introducer sheath assembly of claim 12, wherein a distal end of the tubular plug has a relatively stiff construction as compared to a remainder of the tubular plug.

19. The introducer sheath assembly of claim 12, wherein a distal end of the tubular plug tapers radially inward towards a distal tip of the tubular plug.

20. The introducer sheath assembly of claim 12, wherein the valve comprises an actuator, and wherein the plug comprises a handle releasably coupled to the actuator by an O-ring positioned within an annular recess defined by the actuator.

* * * * *